United States Patent [19]
Robbins

[11] Patent Number: 5,160,576
[45] Date of Patent: Nov. 3, 1992

[54] METHOD OF END POINT DETECTION IN A PLASMA ETCHING PROCESS

[75] Inventor: Michael Robbins, Bethel, Conn.

[73] Assignee: Lam Research Corporation, Fremont, Calif.

[21] Appl. No.: 664,826

[22] Filed: Mar. 5, 1991

[51] Int. Cl.⁵ .............................................. G01N 21/00
[52] U.S. Cl. ................................... 156/626; 156/643; 156/662; 356/357
[58] Field of Search .............. 156/626, 643, 646, 662; 437/7, 8; 204/192.33, 298.32; 356/357, 382

[56] References Cited

U.S. PATENT DOCUMENTS

| | | |
|---|---|---|
| 4,707,611 | 11/1987 | Southwell . |
| 4,826,267 | 5/1989 | Hall et al. . |
| 4,837,044 | 6/1989 | Murarka et al. . |
| 4,913,934 | 4/1990 | Sharp et al. . |
| 4,915,476 | 4/1990 | Hall et al. . |
| 4,936,967 | 6/1990 | Ikuhara et al. ............... 156/626 X |
| 4,952,025 | 8/1990 | Gunning, III . |
| 4,998,021 | 3/1991 | Mimasaka ........................ 156/626 X |

*Primary Examiner*—Thi Dang
*Attorney, Agent, or Firm*—Burns, Doane, Swecker & Mathis

[57] ABSTRACT

A method of optically detecting a change in intensity of an emission peak in a plasma process, such as a plasma etching process, by reflecting an emission spectrum of radiation from the plasma reaction off of a pair of rugate filters. The reflected emission spectrum has increased in-band reflections and decreased out-of-band reflections which provides reduced noise and an easier-to-detect emission peak. The method can be used for endpoint detection in a plasma etching process such as etching of $SiO_2$.

22 Claims, 1 Drawing Sheet

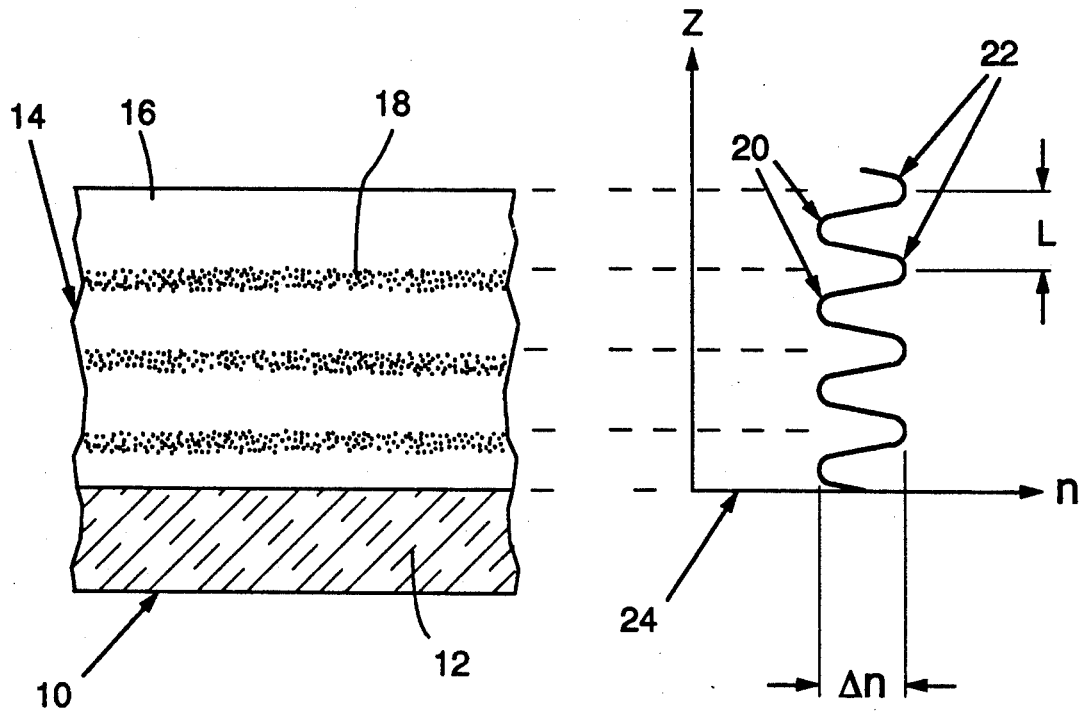
FIG. 1A  FIG. 1B
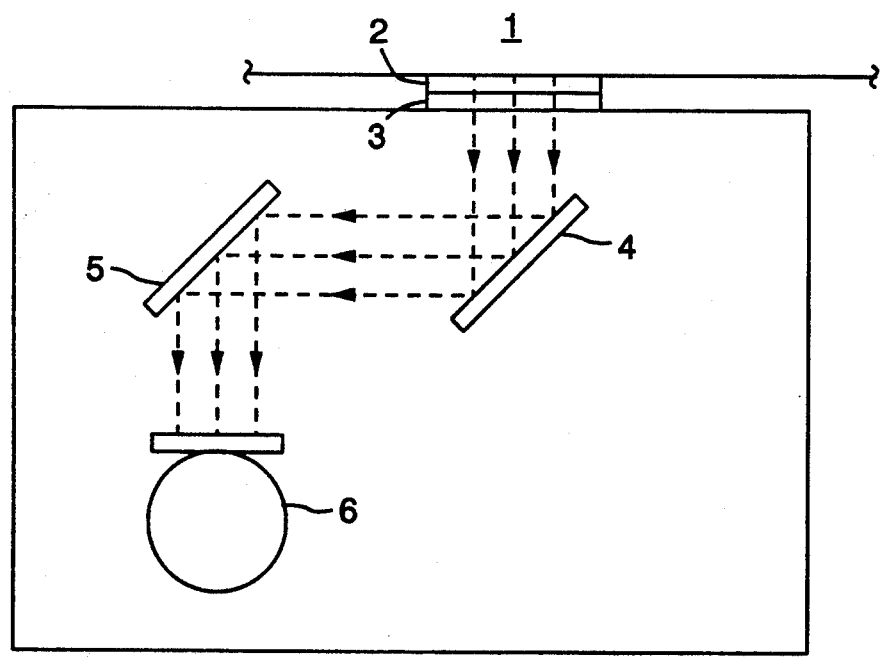
FIG. 2

METHOD OF END POINT DETECTION IN A PLASMA ETCHING PROCESS

BACKGROUND OF THE INVENTION

The present invention relates to an optical detection system for detecting one or more emission peaks generated during a plasma process as well as a method of detecting such emission peaks, particularly in a plasma etching process.

In a silicon dioxide plasma etching process prior to development of the present invention, it was conventional to detect individual emission peaks due to molecular transitions of CO. However, it was not possible to detect the endpoint of a silicon dioxide thin film once the exposed area of the oxide approached approximately 1% (e.g. 99% coverage by a photoresist). One reason for this was that the signal-to-noise ratio was too low.

In conventional detection systems of the above type, a grating was used to filter out all but particular wavelengths. The grating system had many reflective surfaces which permitted only about 50% of the measured radiation to pass therethrough. The radiation which did pass through such a filter was directed into a photomultiplier to multiply the signal by a particular amount such as 100%. The problem with such amplification, however, was that the gain given to the measured signal was also given to the noise. This made it difficult to see a small change in a large signal due to the high level of noise. That is, the noise was multiplied to an extent comparable to the signal being measured. Also, according to the prior art technology, a separate system was used to detect each wavelength. For instance, a separate photodiode and monochromator were used for each system.

Thin-film interference coatings have been employed in antireflection coatings, laser dielectric mirrors, television camera edge filters, band pass filters and stopband filters. Two different materials can be used to fabricate such a composite film such as a relatively high index of refraction material and a relatively low index of refraction material. The two materials can be alternately deposited to specified thicknesses. For instance, discrete layers having intermediate values of refractive index can be provided by coevaporation of two materials or by using a gradient index coating in which the index of refraction within the coating varies continuously as a function of depth. Such gradient index coatings are known in the art as "rugate filters."

Details of rugate filters are described in U.S. Pat. Nos. 4,952,025 ("Gunning"), 4,826,267 ("R. Hall"), 4,837,044 ("Murarka"), 4,915,476 ("J. Hall"), 4,913,934 ("Sharp"), and 4,707,611 ("Southwell"), the disclosures of which are hereby incorporated by reference. In general, rugate filters include a thick film deposited on a substrate (e.g. fused silica). The thick film is deposited in such a way that the refractive index is varied sinusoidally as a function of thickness. To produce a thick film that exhibits multiple frequency reflection peaks, the refractive index profile is a continuously varying, complex sinusoid. The design of the thick film should also take into account the angle of the incidence of a reflected signal.

Gunning discloses that the rugate filter concept was first discovered in the mid-1970's and that such filters make the design of seemingly complex filters much more straightforward. In general, the desired reflected wavelength is directly proportional to the period of a simple sine wave that describes the film refractive index profile. For instance, Gunning points out that to achieve multiple-line rejection filters, the individual sine waves for each wavelength are linearly superimposed in parallel to achieve a multi-sinusoidal refractive index profile that varies with film thickness in a manner that looks complex, but which is easily determined.

As pointed out by Gunning, thin film optical interference filters have been used as antireflection coatings or as highly reflective coatings. For instance, appropriately constructed reflective coatings have been used as narrow bandwidth blocking filters that reflect preselected wavelengths of light, thereby preventing their unwanted transmission through the filter. According to Gunning, gradient-index films can be made by a variety of methods such as by evaporating film materials in a vacuum and then condensing the vapor under very controlled conditions onto the cool surface of the substrate to be coated. Accordingly, bandwidths can be made arbitrarily narrow and sidebands can be greatly reduced.

R. Hall discloses a gradient index spectral filter for placement between an incident medium and a substrate to reflect incident electromagnetic energy having wavelengths within a predetermined band of wavelengths and to transmit incident electromagnetic energy having wavelengths outside of the reflection band. The filter includes a band rejecting portion having a periodic refractive profile ("rugate profile") whose periodicity and amplitude are selected to reflect a maximum amount of electromagnetic energy within the reflection band.

R. Hall discloses that rugate optical coatings are typically fabricated by placing a substrate and one or more source materials in a vacuum chamber, the source materials are heated to increase their vapor pressure and the vacuum chamber pressure is sufficiently reduced that the molecular mean free path is greater than the source-to-target distance, allowing the source materials to deposit on the target surface. Typically, either source can be blocked from access to the target in order to vary the refractive index of the depositing material. The heating of the source material, the choice of the source material, and the duration of the vapor deposition are frequency controlled automatically.

R. Hall discloses that an ellipsometer permits the deposition of ultra thin layers on the order of 100 Å whose thickness can be measured to within a few Å. The ellipsometer measurements can be made in a manner such that the entire film deposition process can be continuously controlled by a computer. Assuming that the two source materials mix cleanly without chemically combining to form new compounds, and assuming that the optical refractive index of the mixed materials is the same as if they were being paired as thin layers, the two materials can be evaporated together in different proportions to form layers with an arbitrary refractive index where the refractive index must be continuously varied so that a gradient index coating can be deposited.

According to R. Hall, it is possible to design a stop-band filter which is specified to reflect wavelengths at 2.0 microns (20,000 Å) and transmit all other wavelengths. The filters of R. Hall are required to operate between an incident medium of air and a glass substrate having a refractive index of 1.52. One of the filters disclosed in R. Hall is an unenhanced rugate filter having 100.5 cycles of sinusoidal variation in its refractive index, a total thickness of 50.2 microns and an optical density within the 2.0 micron rejection band of 3.25.

R. Hall discloses that the side lobes (i.e. out-of-band reflections) can be reduced by (1) adding quarterwave matching layers at both incident and substrate sides of the rugate profile; (2) adding quintic matching layers at each interface; (3) continuing and superimposing the rugate profile on the quintic antireflecting portions of the filter; and (4) providing two back-to-back quintics which are thick enough to superimpose the entire rugate profile on them. R. Hall points out that the rugate design options for the single stop band can also be applied to filters with multiple stopbands and to passband filters. Also, the antireflecting portions for the incident and substrate sides of the filters could be provided at only one of these interfaces or at an interface within a filter, such as between multiple stopband portions of a filter.

Murarka discloses a method of fabricating graded refractive index (rugate) optical filters and complex rugate filters having prespecified refractive index versus thickness profiles. Such optical filter devices typically function in a wavelength range which is at least in part within the visible, near UV and/or near IR electromagnetic spectrum range.

Murarka explains that the attainment of rugate filter bands occurs due to the addition of inphase reflection from multiple layers of varying refractive index. At particular wavelengths, the reflected radiation adds in-phase to provide high transmission or reflection. For high reflectance, the period of the rugate structure should be equal to half the wavelength of the radiation to be reflected. On the other hand, for low reflectance, the period should be equal to the wavelength of the radiation to be transmitted. The width of the spectral range over which high transmission or reflection is to occur increases with the amplitude of the rugate index profile. The magnitude of the transmission or reflectance increases with the index amplitude and number of rugate cycles in the coating.

Murarka discloses a process for fabricating optical filters using interferometers which directly monitor the optical filter throughout the entire deposition process without breaking vacuum. A heterodyning interferometer allows accuracy on the order of Angstroms. The determination of the thickness and refractive index profile for a desired rugate device can be carried out, for example, by Fourier synthesis or sinusoidal design techniques. For instance, computer algorithms can be used to take a desired input spectrum and calculate the closest approximation to the desired optical filter function for the intended spectrum by transforming the index requirement from the frequency to the spatial domain.

According to Murarka, the design of the rugate coating may be defined in terms of four independent parameters: the number of cycles, the average index, the index difference and the period. Accordingly, the performance of a rugate optical filter for particular parameters of the change in peak-to-peak refractive index, number of modulation cycles, peak reflectivity and fractional bandwidth can be maximized for a selected material system.

Murarka discloses that refractive index gradation can be produced by depositing materials of varying composition in which the refractive index is a function of the composition deposited. For example, $ZnS_xSe_{1-x}$ (mixed zinc, sulfide-selenide) provides compositions which can be deposited with a smooth variation in composition between ZnS and ZnSe. Similarly, the silicondioxide nitride system permits deposition of homogeneous compositions which range from substantially pure $SiO_2$ to substantially pure $Si_3N_4$. Another useful system is the aluminum oxide-aluminum nitride system with the compositions and refractive indices which range from substantially pure alumina ($Al_2O_3$) to substantially pure aluminum nitride (AlN). A wide variety of other material systems similarly exhibit an index of refraction variation by stoichiometric variation and may be deposited on a suitable substrate to provide rugate optical devices.

J. Hall discloses a single notch (single band in wavelength) rugate filter manufactured under a monitored and feedback controlled deposition process. The rugate filter of J. Hall is transmissive to optical radiation except near or at a particular notch wavelength wherein the filter is predominantly reflective. The rugate filter of J. Hall was designed to replace multi-layer dielectric filters made of alternating layers of dissimilar materials which had been used to protect optical sensor detection systems from laser radiation damage due to friendly or hostile sources.

The rugate filter of J. Hall includes an epitaxially grown film of aluminum-gallium-arsenide (Al-Ga-As). The film can be optically monitored by reflecting a beam from the film at a perpendicular or known angle of incidence to an optical thickness detector system. Alternatively, the beam can be transmitted through the film to the detector system. The detector system generates output signals which are a function of the light beam intensity.

FIG. 1 shows a cross-sectional view of a conventional ideal, sinusoidal rugate filter profile taken along the film thickness direction (z). Rugate filter 10 is comprised of a compositionally uniform optically transmissive substrate material 12, upon which a graded-index, optical medium 14 is coated. Medium 14 exhibits a continuously varying graded index as depicted by the alternating and continuous optical index profile regions 16 and 18. Regions 16 and 18, respectively, emulate gradation of index troughs 20 and peaks 22 which are associated with a periodic, sinusoidal design as shown by the graph 24. Graph 24 plots refractive index (n) against film thickness in the z direction. The sinusoidal index profile is a spectrally pure form of periodic structure that will produce a predominant Bragg reflection at a single, narrow wavelength band. The term "Bragg reflection" refers to the fact that a periodic structure of the rugate filter follows Bragg's Law which predicts that there will be a reflectance maximum in wavelength at the "notch wavelength". The notch wavelength can be varied as a function of the average index of refraction over one period in film thickness, the physical length of periodicity or one cycle in film thickness along the z axis and the angle of incidence of radiation as measured from the perpendicular to the surface.

The rugate filter of J. Hall is made by a metal-organic chemical vapor deposition (MOCVD) process which produces an optical coating in the form of a single crystal $Al_xGa_{1-x}As$. The Al and Ga fractions of the epitaxial layer are modulated to produce the refractive index profile of a rugate filter which can be generated with refractive index control between about 2.9 and 3.3 since the refractive index varies with the fraction x for $Al_xGa_{1-x}As$.

Other methods of making such a layer of optical material include other thermal chemical vapor deposition processes, photochemical vapor deposition, thermal evaporation or physical vapor deposition, electron beam evaporation, sputter deposition and molecular beam epitaxial growth. J. Hall discloses that a notch at 4 microns in wavelength can be obtained by providing the $Al_xGa_{1-x}As$ film with just over 15 periods in a 10 micron targeted film thickness. With the metal-organic process, concentrations of precursors such as trimethyl gallium and trimethyl aluminum in a background of arsine and hydrogen can be controlled.

J. Hall points out that optical monitoring of the deposition process can be performed by means of an optical monitoring signal (such as a single-wavelength reflectance at normal incidence with a monitor wavelength at one-half of the notch wavelength) superimposed on the refractive index profile. Accurate, incremental optical thickness signals are measured by standard and conventional means since interference minima and maxima occur at every quarter-wave increment of optical thickness relative to a reflected or transmitted monitoring wavelength. In particular, the monitor beam is at the notch wavelength or at one-half the notch wavelength. One-half the notch wavelength provides twice as many corrective opportunities per period compared to monitoring at the notch wavelength.

J. Hall discloses a conventional detection system used to obtain optical thickness increments of a deposited film having a rugate filter profile. In particular, light is filtered through a scannable monocromator either at a monitor beam source or at a detector which sets the monitor wavelength. A sample is held within a chamber and light from the monitor beam source is reflected from a mirror onto the sample and onto another mirror for output to an external control system. A reflected monitor beam detector receives the light from the sample and converts the optical input signal to determine optical thickness increments with a signal processor.

Southwell discloses that the optical properties of a rugate filter are determined by the values of $n_a$ (the average refractive index) and $n_p$ (the index modulation). The width of the reflection band for such filters is proportional to $n_p/n_a$ and the peak value of the reflectance is determined by $N(n_p/n_a)$ where N is the number of sinusoidal periods in the filter. Accordingly, high reflectivity can be maintained within a narrow bandwidth by increasing the number of periods in the rugate filter structure.

SUMMARY OF THE INVENTION

The present invention provides a method of end-point detection in a plasma etching process wherein a specimen is etched by means of glow discharge in a reaction chamber. The method includes detecting the intensity of at least one emission peak in an emission spectrum of radiation from the glow discharge. The emission spectrum is reflected from at least one rugate filter prior to measuring the intensity of the emission peak in the emission spectrum. The emission spectrum is preferably reflected from the rugate filter to a second rugate filter prior to detecting the intensity of the emission peak in the emission spectrum. The angle of incidence between the emission spectrum and a normal to each rugate filter should be set at a value which achieves suitable reflection. The angle of incidence can be in the range of 5° to 85° or in the range of 30° to 60°. For instance, the angle could be about 45°.

A plurality of emission peaks can be optically measured according to the method of the invention. In this case, the rugate filter filters the emission spectrum such that a plurality of bandwidths are reflected therefrom. Each of the bandwidths includes a respective one of the emission peaks.

The emission spectrum can be passed through a window in the reaction chamber and/or at least one edge filter prior to being reflected by the rugate filter. It is preferable, however, to pass the emission spectrum through a collimating lens prior to being reflected by the rugate filter. After being reflected by the rugate filter, the emission spectrum can be passed into an amplification device such as a photomultiplier, photodiode, etc.

The emission peak can be produced by an etching reaction. For instance, if the specimen comprises an exposed surface of silicon dioxide, the emission peak can be produced by a molecular transition of a CO molecule. Of course, specimens of other materials will produce other detectable molecular transitions. The method is effective in end-point detection even when the exposed surface is no greater than 1% of a total surface area of the specimen.

The invention also provides a method of optically detecting an intensity change of an emission peak in a plasma process. The method includes providing a plasma reaction by reacting plasma reactants with a surface of a specimen in a reaction chamber, reflecting an emission spectrum of radiation from the plasma reaction off at least one rugate filter and optically detecting an intensity of at least one emission peak in the emission spectrum reflected off of the rugate filter.

The emission spectrum is preferably reflected from the rugate filter to a second rugate filter prior to detecting the intensity of the emission peak in the emission spectrum. A plurality of emission peaks can be optically detected by using a rugate filter which can reflect a plurality of bandwidths, each of the bandwidths including a respective one of the emission peaks. The emission spectrum can be passed through a window in the reaction chamber and/or at least one edge filter prior to being reflected by the rugate filter. Preferably, the emission spectrum is passed through a collimating lens prior to being reflected by the rugate filter. The intensity of the emission peak in the emission spectrum can be detected by passing the emission spectrum into a photomultiplier.

The invention also provides an optical detection system which includes directing means for directing an emission spectrum of radiation in an axial direction, filter means for filtering and reflecting the emission spectrum and detecting means for optically detecting an intensity of at least one emission peak in the in-band reflections of the reflected beam of radiation. A pass-through beam of radiation having wavelengths above and below a target bandwidth passes through the filter means and a reflected beam of radiation having in-band reflections within the target bandwidth and out-of-band reflections above and below the target bandwidth is reflected from the filter means. The filter means is effective to reflect a higher percentage of the in-band reflections than the out-of-band reflections so that in-band reflectivity is increased and noise is reduced.

The filter means can comprise at least one rugate filter. Preferably, the filter means comprises a pair of spaced-apart rugate filters. For instance, the filter means can comprise a rugate filter oriented with respect to the axial direction such that the emission spectrum is incident on a surface of the rugate filter at an angle between the emission spectrum and a normal to the rugate surface which achieves suitable reflection. For instance, the angle could in the range of 5° to 85° or 30° to 60°. As an example, the angle could be about 45°. When two rugate filters are used, the rugate filters can have reflecting surfaces which are parallel to each other.

The rugate filter can be designed to filter the emission spectrum such that a plurality of target bandwidths are reflected therefrom, each of the bandwidths including a respective one of the emission peaks.

The directing means can comprise a collimating lens and/or a window of a plasma reaction chamber. The directing means can also comprise an edge filter which filters out wavelengths of the emission spectrum below the target bandwidth. For instance, the directing means can comprise a pair of edge filters which filter out wavelengths of the emission spectrum above and below the target bandwidth.

BRIEF DESCRIPTION OF THE DRAWINGS

The invention will now be described with reference to the drawing, in which:

FIG. 1 shows a conventional ideal schematic sinusoidal rugate profile versus film growth of an optically active medium coated on a substrate; and FIG. 2 shows an optical detection system in accordance with the invention.

DETAILED DESCRIPTION OF THE PREFERRED EMBODIMENTS

The invention overcomes a problem in endpoint detection in processes where the emission signal being observed becomes undetectable. Such a problem occurs when contact holes or vias in silicon dioxide are etched by glow discharge. This problem is particularly troublesome as the exposed area of silicon dioxide becomes very low. For instance, as the exposed area of silicon dioxide approaches approximately 1% or less, the amount of amplitude change, at endpoint, in the emission signal being observed (typically 4835 Å CO emission) becomes undetectable. The reason for this is that the size of the amplitude change becomes comparable to the noise as the amount of exposed oxide decreases.

According to one aspect of the invention, at least one emission peak is detected optically. In particular, more than one wavelength (emission peak) is detected and at least one rugate filter is used to reflect and multiply the detected in-band wavelengths while reducing out-of-band reflections.

During a plasma reaction, such as plasma etching, photons are given off when a molecular transition occurs. The photons are at one or more characteristic wavelengths for a particular molecular transition. Such characteristic wavelengths are referred to herein as "emission peaks." One or more of the emission peaks are used according to the invention to detect operating conditions in a plasma process such as a plasma etching process. For instance, such a plasma etching process could use Ar, $CF_4$ and $CHF_3$ gases in the plasma reaction chamber. During etching, when a molecular transition of CO occurs, photons at several characteristic wavelengths are given off. In fact, all transitions of the CO molecule give information. This information is detected using at least one rugate filter in accordance with the invention. For instance, when the etching process is completed, the activity of the molecular transition of CO changes and can be detected with the optical detection system according to the invention.

According to a further aspect of the invention, several emission peaks can be integrated to provide an amplitude change at end-point which is greater than in a single wavelength detection system. In addition, by reflecting the integrated signal off at least one rugate filter, the signal-to-noise ratio can be maintained at a high level. By reflecting the integrated signal off two separate rugate filters, the signal-to-noise ratio entering an amplification device such as a photomultiplier, photodiode, etc. could be as high as 81 to 1 with 90% in-band reflection off of each of the rugates.

The invention is applicable to processes other than plasma etching. For instance, endpoint detection can be carried out in processes previously unable to utilize endpoint detection. One such process is the tapered via process which employs resist erosion by the addition of oxygen. By identifying the appropriate emission peaks (e.g. using a multichannel analyzer) of etching by-products, a rugate filter can be designed to provide a usable endpoint signal. The optical detection system in accordance with the invention may also be useful for other detection systems such as real-time deposition rate monitors or impurity monitors.

FIG. 2 shows schematically how at least one selected emission peak from an emission spectrum can be arithmetically added together in accordance with the invention. In particular, radiation passes from chamber 1, through chamber window/edge filters 2, through collimating lens 3 and is reflected by a pair of rugate filters 4, 5 into photomultiplier 6. This arrangement allows several of the more prominent in-band emission peaks to be added together while substantially filtering out all other out-of-band wavelengths. For instance, in the case of etching $SiO_2$, emission peaks due to Ar are above and below the target band for CO emissions. Such Ar emissions are close enough to the in-band wavelength that false readings in detection of CO emissions can occur. However, such Ar emissions can be effectively filtered out with an edge filter and/or the rugate filters in accordance with the invention. Accordingly, the integrated intensity should be capable of producing an amplitude change at endpoint which is distinguishable from the noise.

Edge filters 2 can comprise a pair of filters which eliminate wavelengths above and below the area of interest. If only a single edge filter is used, it is preferable to filter out wavelengths below the in-band target range. This will avoid potential higher order harmonic frequencies caused by frequencies below the in-band target range. The high order harmonic frequencies could cause false readings in detecting the CO emissions. Collimating lens 3 insures that all illumination incident on rugate filter 4 is parallel. The combination of the collimating lens with the rugate filters greatly enhances the effectiveness of the optical detection system of the invention in reducing noise and increasing the signal-to-noise ratio.

One or more rugate filters can be used in accordance with the invention. However, it is preferable to use two rugate filters. This will increase the signal-to-noise ratio without unduly lowering the intensity of the in-band reflections. That is, although the signal-to-noise ratio can be increased with each reflection off a rugate filter, each reflection also causes reduction in the intensity of the signal to be measured.

When used in a SiO$_2$ plasma etching process, the optical detection system according to the invention can be used for detecting any or all of the following emission peaks for CO: 4510.9 Å, 4835.3 Å, 5198.2 Å, 5610.2 Å and 6079.9 Å. These peaks are identified by R. W. B. Pearse and A. G. Gaydon in the *Identification of Molecular Spectra*, 3rd Ed., (Wiley & Sons 1963), page 115. The rugate filter arrangement according to the invention allows a plurality of emission peaks to be added together to produce an amplitude change at endpoint which is distinguishable from the noise measured in the detected signal.

The rugate filter system according to the invention can provide a narrow band of in-band target reflections, of the selected emission peaks, of about 90% maximum whereas the out-of-band reflectivities are typically about 10%. Theoretically, by utilizing two rugate filters having a 90% reflectivity of the in-band wavelengths and a 10% reflectivity of the out-ofband wavelengths, the net in-band reflectivity would be 0.9×0.9=81% whereas the net out-of-band reflectivity would be 0.1×0.1=1%. Accordingly, the change at endpoint can be increased and by optically achieving a signal to noise ratio of 81:1, the goal of low exposed area endpoints can be attained.

While the invention has been described with reference to the foregoing embodiments, various changes and modifications can be made thereto which fall within the scope of the appended claims.

What is claimed is:

1. A method of end-point detection in a plasma etching process, comprising:
   etching a specimen by means of glow discharge in a reaction chamber; and
   optically detecting an intensity of at least one emission peak in emission spectrum of radiation from the glow discharge, the emission spectrum being reflected from at least one rugate filter prior to measuring the intensity of the emission peak in the emission spectrum.

2. The method of claim 1, wherein the emission spectrum is reflected from the one rugate filter to a second rugate filter prior to detecting the intensity of the emission peak in the emission spectrum.

3. The method of claim 1, wherein a plurality of emission peaks are optically measured, the rugate filter filtering the emission spectrum such that a plurality of bandwidths are reflected therefrom, each of the bandwidths including a respective one of the emission peaks.

4. The method of claim 1, wherein the emission spectrum is passed through a window in the reaction chamber prior to being reflected by the rugate filter.

5. The method of claim 1, wherein the emission spectrum is passed through at least one edge filter prior to being reflected by the rugate filter.

6. The method of claim 1, wherein the emission spectrum is passed through a collimating lens prior to being reflected by the rugate filter.

7. The method of claim 1, wherein the emission spectrum is passed into amplification means for amplifying the intensity of the emission peak after the emission peak is reflected by the rugate filter.

8. The method of claim 1, wherein the emission peak is produced by an etching reaction.

9. The method of claim 1, wherein the specimen comprises an exposed surface of silicon dioxide and the emission peak is produced by a molecular transition of a CO molecule.

10. The method of claim 9, wherein the exposed surface is no greater than 1% of a total surface area of the specimen.

11. The method of claim 3, wherein the emission peaks are produced by molecular transitions of at least one etching reaction product.

12. The method of claim 1, further comprising a step of adjusting an angle of incidence between the emission spectrum and a normal to a reflecting surface of the rugate filter such that suitable reflection of the emission spectrum is achieved.

13. The method of claim 12, wherein the rugate filter is oriented such that the angle of incidence is about 45°.

14. A method of optically detecting a change in intensity of an emission peak in a plasma process, comprising:
    providing a plasma reaction by reacting a plasma reactant with a surface of a specimen in a reaction chamber;
    reflecting an emission spectrum of radiation from the plasma reaction off at least one rugate filter; and
    optically detecting an intensity of at least one emission peak in the emission sppeotrum refleoted off of the rugate filter.

15. The method of claim 14, wherein the emission spectrum is reflected from the one rugate filter to a second rugate filter prior to detecting the intensity of the emission peak in the emission spectrum.

16. The method of claim 14, wherein a plurality of emission peaks are optically detected, the rugate filter filtering the emission spectrum such that a plurality of bandwidths are reflected therefrom, each of the bandwidths including a respective one of the emission peaks.

17. The method of claim 14, wherein the emission spectrum is passed through a window in the reaction chamber prior to being reflected by the rugate filter.

18. The method of claim 14, wherein the emission spectrum is passed through at least one edge filter prior to being reflected by the rugate filter.

19. The method of claim 14, wherein the emission spectrum is passed through a collimating lens prior to being reflected by the rugate filter.

20. The method of claim 14, wherein the intensity of the emission peak in the emission spectrum is detected by passing the emission spectrum into a photomultiplier.

21. The method of claim 14, further comprising a step of adjusting an angle of incidence between the emission spectrum and a normal to a reflecting surface of the rugate filter such that suitable reflection of the emission spectrum is achieved.

22. The method of claim 14, wherein the rugate filter is oriented such that the angle of incidence is about 45°.

* * * * *

UNITED STATES PATENT AND TRADEMARK OFFICE
CERTIFICATE OF CORRECTION

PATENT NO. : 5,160,576

DATED : November 3, 1992

INVENTOR(S) : Michael Robbins

It is certified that error appears in the above-identified patent and that said Letters Patent is hereby corrected as shown below:

Column 10, line 30, delete "speotrum" and insert --spectrum-- therefor.

Signed and Sealed this

Twenty-first Day of December, 1993

Attest:

BRUCE LEHMAN

*Attesting Officer*  *Commissioner of Patents and Trademarks*